(12) United States Patent
Vignon et al.

(10) Patent No.: US 11,529,125 B2
(45) Date of Patent: Dec. 20, 2022

(54) METHODS AND SYSTEMS FOR PROCESSING AN ULTRASOUND IMAGE

(71) Applicant: KONINKLIJKE PHILIPS N.V., Eindhoven (NL)

(72) Inventors: Francois Guy Gerard Marie Vignon, Andover, MA (US); Jun Seob Shin, Medford, MA (US); Sheng-Wen Huang, Ossining, NY (US); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 319 days.

(21) Appl. No.: 16/622,101

(22) PCT Filed: Jun. 13, 2018

(86) PCT No.: PCT/EP2018/065720
§ 371 (c)(1),
(2) Date: Dec. 12, 2019

(87) PCT Pub. No.: WO2018/229159
PCT Pub. Date: Dec. 20, 2018

(65) Prior Publication Data
US 2020/0121295 A1 Apr. 23, 2020

Related U.S. Application Data

(60) Provisional application No. 62/520,174, filed on Jun. 15, 2017.

(30) Foreign Application Priority Data

Jul. 6, 2017 (EP) .................................... 17180090

(51) Int. Cl.
A61B 8/08 (2006.01)
G06T 7/00 (2017.01)

(52) U.S. Cl.
CPC .......... *A61B 8/5276* (2013.01); *A61B 8/5207* (2013.01); *G06T 7/0012* (2013.01);
(Continued)

(58) Field of Classification Search
None
See application file for complete search history.

(56) References Cited

U.S. PATENT DOCUMENTS 5,706,818 A 1/1998 Gondo
2002/0169378 A1 11/2002 Mo et al.
(Continued)

FOREIGN PATENT DOCUMENTS

JP H06327682 A 11/1994
JP 2005205198 A 8/2005

OTHER PUBLICATIONS

Byram, B. (Mar. 2013). Ultrasonic reverberation and off-axis clutter suppression using aperture domain signal decomposition. In Medical Imaging 2013: Ultrasonic Imaging, Tomography, and Therapy (vol. 8675, pp. 236-244). SPIE. (Year: 2013).*
(Continued)

Primary Examiner — Samah A Beg

(57) ABSTRACT

The invention provides methods and systems for generating an ultrasound image. In a method, the generation of an ultrasound image comprises: obtaining channel data, the channel data defining a set of imaged points; for each imaged point: isolating the channel data; performing a spatial spectral estimation on the isolated channel data; and selectively attenuating the spatial spectral estimation channel data, thereby generating filtered channel data; and summing the filtered channel data, thereby forming a filtered
(Continued)

ultrasound image. In some examples, the method comprises aperture extrapolation. The aperture extrapolation improves the lateral resolution of the ultrasound image. In other examples, the method comprises transmit extrapolation. The transmit extrapolation improves the contrast of the image. In addition, the transmit extrapolation improves the frame rate and reduces the motion artifacts in the ultrasound image. In further examples, the aperture and transmit extrapolations may be combined.

15 Claims, 14 Drawing Sheets

(52) U.S. Cl.
CPC .............. *G06T 2207/10132* (2013.01); *G06T 2207/20024* (2013.01); *G06T 2207/20182* (2013.01)

(56) References Cited

U.S. PATENT DOCUMENTS

| | | | |
|---|---|---|---|
| 2003/0199764 A1* | 10/2003 | Kim .................. | A61B 8/06 600/437 |
| 2005/0033165 A1 | 2/2005 | Ustuner et al. | |
| 2006/0140465 A1 | 6/2006 | Sato | |
| 2009/0259706 A1 | 10/2009 | Wu et al. | |
| 2011/0218439 A1* | 9/2011 | Masui ................. | A61B 8/08 600/443 |
| 2011/0309971 A1 | 12/2011 | Kanamoto | |
| 2014/0219050 A1* | 8/2014 | Park .................. | G01N 29/4418 382/173 |
| 2014/0316274 A1 | 10/2014 | Koh et al. | |
| 2019/0369220 A1* | 12/2019 | Vignon ............... | G01S 15/8977 |
| 2021/0124043 A1* | 4/2021 | Long .................. | A61B 8/5223 |

OTHER PUBLICATIONS

Jeong, M. K. (2000). A Fourier transform-based sidelobe reduction method in ultrasound imaging. IEEE transactions on ultrasonics, ferroelectrics, and frequency control, 47(3), 759-763. (Year: 2000).*

Yipeng, D., Wei, W., & Guangyou, F. (Oct. 2011). Through-wall tracking of human movers using joint slope-demodulation and adaptive filter processing. In 2011 First International Conference on Instrumentation, Measurement, Computer, Communication and Control (pp. 630-634). IEEE. (Year: 2011).*

Shin, et al., "Spatial Prediction Filtering of Acoustic Clutter and Random Noise in Medical Ultrasound Imaging", IEEE Transactions on Medical Imaging, vol. 36, No. 2, Feb. 2017, pp. 396-406.

International Search and Written Opinion for International Application No. PCT/EP2018/065720, filed Jun. 13, 2018, 18 pages.

Krishnan, et al., "Adaptive Aberration Correction of Abdominal Images Using PARCA", Ultrasonic Imaging 19,169-179 (1997) (Abstract).

Byram, et al., "A model and regularization scheme for ultrasonic beamforming clutter reduction", IEEE Transactions on Ultrasonics, Ferroelectrics, and Frequency Control, vol. 62, Issue: 11, Nov. 2015 (Abstract).

David, et al., "Time Domain compressive beamforming of ultrasound signals" J. Acoust. Soc. Am. 137 (5), May 2015, pp. 2273-2784.

* cited by examiner 500   510   520

METHODS AND SYSTEMS FOR PROCESSING AN ULTRASOUND IMAGE

RELATED APPLICATIONS

This application is the U.S. National Phase application under 35 U.S.C. § 371 of International Application No. PCT/EP2018/065720, filed on Jun. 13, 2018, which claims the benefit of and priority to European Application No. 17180090.7, filed Jul. 6, 2017, and Provisional Application Ser. No. 62/520,174, filed Jun. 15, 2017. These applications are hereby incorporated in their entirety by reference herein.

FIELD OF THE INVENTION

This invention relates to the field of ultrasound imaging, and more specifically to the field of ultrasound image filtering.

BACKGROUND OF THE INVENTION

Ultrasound imaging is increasingly being employed in a variety of different applications. It is important that the image produced by the ultrasound system is as clear and accurate as possible so as to give the user a realistic interpretation of the subject being scanned. This is especially the case when the subject in question is a patient undergoing a medical ultrasound scan. In this situation, the ability of a doctor to make an accurate diagnosis is dependent on the quality of the image produced by the ultrasound system.

Off-axis clutter is a significant cause of image degradation in ultrasound. Adaptive beamforming techniques, such as minimum variance (MV) beamforming, have been developed and applied to ultrasound imaging to achieve an improvement in image quality; however, MV beamforming is computationally intensive as an inversion of the spatial covariance matrix is required for each pixel of the image. In addition, even though MV beamforming is developed primarily for an improvement in spatial resolution, and is not ideal for reducing off-axis clutter, its performance in terms of improving spatial resolution often needs to be sacrificed by reducing the subarray size. Otherwise, image artifacts may occur in the speckle due to signal cancellation.

Adaptive weighting techniques, such as: the coherence factor (CF); the generalized coherence factor (GCF); the phase coherence factor (PCF); and the short-lag spatial coherence (SLSC), have been proposed but all require access to per-channel data to compute a weighting mask to be applied to the image. Further, these methods would only work for conventional imaging with focused transmit beams and are not suitable for plane wave imaging (PWI) or diverging wave imaging (DWI) involving only a few transmits.

In addition, spatial resolution in ultrasound images, particularly the lateral resolution, is often suboptimal. The −6 dB lateral beamwidth at the focal depth is determined by the following equation:

$$-6 \text{ dB } Beamwidth_{lateral} = \frac{\lambda z}{D}$$

where $\lambda$ is wavelength, z is transmit focal depth, and D is the aperture size. The smaller the wavelength (or the higher center frequency), the better the lateral resolution will be; however, a smaller wavelength is achieved at the cost of penetration depth. On the other hand, a larger aperture size D is needed to achieve a better lateral resolution; however, the aperture size is often limited by the human anatomy, hardware considerations, and system cost.

Adaptive beamforming techniques, such as the previously mentioned minimum variance (MV) beamforming, have been a topic of active research. These methods are data-dependent beamforming methods that seek to adaptively estimate the apodization function that yields lateral resolution beyond the diffraction limit.

In addition to standard ultrasound imaging techniques, plane wave imaging (PWI) or diverging wave imaging (DWI) in the case of phased arrays is a relatively new imaging technique, which has the potential to perform imaging at very high frame rates above 1 kHz and possibly several kHz. These techniques have also opened up many new possible imaging modes for different applications which were previously not possible with conventional focused transmit beams. For this reason, they have been some of the most actively researched topics in academia in recent years.

PWI/DWI can achieve high frame rates by coherently compounding images obtained from broad transmit beams at different angles. Since the spatial resolution in PWI/DWI is generally known to be only slightly worse than, or comparable to, conventional imaging with focused transmit beams, its main drawback is degradation in the image contrast, which is directly related to the number of transmit angles. The image contrast is generally low for a small number of transmit angles in PWI/DWI; therefore, many transmit angles are needed to maintain image quality comparable to that of conventional imaging with focused transmit beams.

PWI/DWI also suffers from motion artifacts, particularly when imaging fast-moving organs such as the heart, as individual image pixels are constructed from signals from different transmit beams. The effect of motion becomes more severe with increasing numbers of transmit angles; therefore, the dilemma in PWI/DWI systems is clear: more transmit angles are required to achieve high image contrast, but also result in more motion artifacts that degrade image quality.

Further, regardless of the number of transmit angles, PWI/DWI does not reduce reverberation clutter, which is one of the main sources of image quality degradation in fundamental B-mode ultrasound images.

Document US 2005/033165 A1 describes technique for adaptive suppression of the grating lobe in ultrasound imaging, in which processing of received ultrasound data is altered depending on the detection of an excessive grating lobe energy. In particular, the gain of the individual transducer elements in a receive beamformer is modulated as a function of any detected grating lobe energy.

On the other hand, in US 2014/316274 A1 it is disclosed a clutter filtering method that includes transmitting an ultrasound signal to an object, receiving a reflection signal reflected from the object, performing a singular value decomposition (SVD) on a plurality of Doppler signals constituting the reflection signal, dividing a representation of the object into a plurality of regions according to a result of performing the SVD, determining cutoff frequencies of the plurality of regions according to different methods, and performing clutter filtering on the plurality of regions by using the determined cutoff frequencies.

There is therefore a need for a means of performing off-axis clutter filtering within an ultrasound system without requiring significant additional hardware. In addition, there is a need for a means of improving spatial resolution of an ultrasound image without requiring significant additional hardware. There is also a need for a means of improving image contrast in an ultrasound system without requiring significant additional hardware.

SUMMARY OF THE INVENTION

The invention is defined by the claims.

According to examples in accordance with an aspect of the invention, there is provided a method for performing off-axis clutter filtering in an ultrasound image, the method comprising:

obtaining channel data from an ultrasonic probe defining a set of imaged points, wherein the ultrasonic probe comprises an array of transducer elements;
for each imaged point in a region of interest:
isolating the channel data associated with said imaged point;
performing a spatial spectral estimation of the isolated channel data to identify one or more spatial-frequency components of the isolated channel data; and
selectively attenuating the one or more spatial-frequency components of the isolated channel data by way of an attenuation coefficient based on the spatial spectral estimation, thereby generating filtered channel data; and
summing the filtered channel data associated with each imaged point of said set of imaged points, thereby generating a filtered ultrasound image.

This method performs off-axis clutter filtering in an ultrasound image. By performing a spatial spectral estimation of the channel data it is possible to identify the frequency content (i.e., one or more spatial-frequency components) of the isolated channel data. Typically, off-axis clutter signal will possess a high spatial frequency, which may be identified in the spatial spectral estimation of the channel data. In this way, it is possible to selectively attenuate signals having high spatial frequencies, thereby reducing and/or eliminating off-axis clutter signals in the final ultrasound image.

Each imaged point of the set of image points is preferably an axial segment of the channel data.

Preferably, the isolating of the channel data is based on axial imaging depth of the channel data.

In an embodiment, the isolating of the channel data comprises processing a plurality of observations of the imaged point.

In this way, it is possible to perform the spatial spectral estimation on channel data that has been averaged over a plurality of measurements. In this way, the accuracy of the channel data, and so of the final ultrasound image, is increased.

In an arrangement, the spatial spectral estimation comprises decomposing the channel data into a finite sum of complex exponentials.

By decomposing the channel data into a finite sum of complex exponentials, it is simple to identify the components with high spatial frequencies, thereby making it easier to attenuate the off-axis clutter signals in the ultrasound image.

In a further arrangement, the complex exponentials comprise:
a first model parameter; and
a second model parameter.

In a further embodiment, the first model parameter is complex.

In a yet further embodiment, the second model parameter is inversely proportional to the distance between adjacent transducer elements of the ultrasonic probe.

The first and second model parameters may be used to describe the nature of the channel data. In the case that the first model parameter is complex, the imaginary component relates to the phase of the signals and the modulus, which may be a real, positive number, relates to the amplitude of the signal. The second model parameter may relate to the spatial frequency of the signal.

In a still yet further arrangement, the first and second model parameters are estimated by way of spatial spectral estimation.

In some designs, the attenuation coefficient is Gaussian.

In this way, it is simple to implement attenuation for signals approaching higher spatial frequencies. The aggressiveness of the filtering may be tuned by altering the width of the Gaussian used.

In an embodiment, the attenuation coefficient is depth dependent.

By making the attenuation coefficient depth dependent, it is possible to control the amount of off-axis clutter signal filtering for different depths.

In an arrangement, the attenuation coefficient is dependent on the second model parameter.

In this way, the attenuation coefficient may be directly dependent on the spatial frequency of the signal, meaning that the attenuation coefficient may adapt to the signals on an individual basis rather than requiring an input from the user.

In some embodiments, the attenuation coefficient is adapted to attenuate the channel data to half the width of the receive beampattern.

In this way, it is possible to both improve the lateral resolution and decrease the off-axis clutter in the filtered ultrasound image.

In some arrangements, the spatial spectral estimation is based on an autoregressive model.

According to examples in accordance with a further aspect of the invention, there is provided a computer program comprising computer program code means which is adapted, when said computer program is run on a computer, to implement the method described above.

According to examples in accordance with a further aspect of the invention, there is provided a controller for controlling the filtering of off-axis clutter in an ultrasound image, wherein the controller is adapted to:

obtain channel data from an ultrasonic probe defining a set of imaged points;
for each imaged point in a region of interest:
isolate the channel data associated with said imaged point;
perform a spatial spectral estimation of the isolated channel data to identify one or more spatial-frequency components of the isolated channel data; and
selectively attenuate the one or more spatial-frequency components of the isolated channel data by way of an attenuation coefficient based on the spatial spectral estimation, thereby generating filtered channel data; and
sum the filtered channel data associated with each imaged point of said set of imaged points, thereby generating a filtered ultrasound image.

According to examples in accordance with a further aspect of the invention, there is provided an ultrasound system, the system comprising:
an ultrasonic probe, the ultrasonic probe comprising an array of transducer elements;
a controller as defined above; and a display device for displaying the filtered ultrasound image.

According to examples in accordance with a further aspect of the invention, there is provided a method for generating an ultrasound image, the method comprising:
  obtaining channel data by way of an ultrasonic probe;
  for each channel of the channel data, segmenting the channel data based on an axial imaging depth of the channel data;
    for each segment of the segmented channel data:
      estimating an extrapolation filter based on the segmented channel data, the extrapolation filter having a filter order; and
      extrapolating, by an extrapolation factor, the segmented channel data based on the extrapolation filter, thereby generating extrapolated channel data; and
    summing the extrapolated channel data across all segments, thereby generating the ultrasound image.

This method performs aperture extrapolation on the channel data, thereby increasing the lateral resolution of the ultrasound image. By estimating the extrapolation filter based on the segmented channel data, the extrapolation filter may directly correspond to the channel data. In this way, the accuracy of the extrapolation performed on the segmented channel data is increased. In other words, this method predicts channel data from transducer elements that do not physically exist within the ultrasonic probe by extrapolating the existing channel data.

In an embodiment, the method further comprises:
  for each axial segment of the channel data, applying a Fourier transform to an axial segment of the channel data; and
  performing an inverse Fourier transform on the extrapolated channel data.

By performing the extrapolation of the segmented channel data in the temporal frequency domain, the accuracy of the extrapolated channel data may be further increased.

In an arrangement, the axial segment is less than 4 wavelengths in depth, for example less than or equal to 2 wavelengths in depth.

In this way, the performance of the system, which is largely dependent on the number of segments of channel data to be extrapolated, may be improved whilst maintaining the improvement in lateral resolution of the image, which is inversely proportional to the size of the axial segment.

In an embodiment, the extrapolation factor is less than or equal to 10×, for example less than or equal to 8×.

In this way, it is possible to achieve a substantial improvement in the lateral resolution of the ultrasound image whilst preserving the speckle texture within the image.

In some designs, the estimation of the extrapolation filter is performed using an autoregressive model.

In an arrangement, the estimation of the extrapolation filter is performed using the Burg technique.

In this way, the extrapolation filter may be simply estimated without requiring a significant amount of processing power.

In some embodiments, the filter order is less than or equal to 5, for example less than or equal to 4.

In this way, it is possible to achieve a substantial improvement in the lateral resolution of the ultrasound image whilst preserving the speckle texture within the image.

In an embodiment, the extrapolation occurs in the azimuthal direction in the aperture domain.

According to examples in accordance with a further aspect of the invention, there is provided a computer program comprising computer program code means which is adapted, when said computer program is run on a computer, to implement the method defined above.

According to examples in accordance with a further aspect of the invention, there is provided a controller for controlling the generation of an ultrasound image, wherein the controller is adapted to:
  obtain channel data by way of an ultrasonic probe;
  for each channel of the channel data, segment the channel data based on an axial imaging depth of the channel data;
    for each segment of the segmented channel data:
      estimate an extrapolation filter based on the segmented channel data, the extrapolation filter having a filter order; and
      extrapolate, by an extrapolation factor, the segmented channel data based on the extrapolation filter, thereby generating extrapolated channel data; and
    sum the extrapolated channel data across all segments, thereby generating the ultrasound image.

According to examples in accordance with a further aspect of the invention, there is provided an ultrasound system, the system comprising:
  an ultrasonic probe;
  a controller as defined above; and
  a display device for displaying the ultrasound image.

In an embodiment, the system further comprises a user interface having a user input.

In this way, it is possible for a user to provide an instruction to the ultrasound system.

In an arrangement, the user input is adapted to adjust the axial depth of the axial segment.

In a further arrangement, the user input is adapted to alter the extrapolation factor.

In a yet further arrangement, the user input is adapted to alter the filter order.

In this way, the user may empirically adapt the various parameters of the extrapolation method in order to maximize the image quality according to their subjective opinion.

According to examples in accordance with a yet aspect of the invention, there is provided a method for generating an ultrasound image, the method comprising:
  obtaining beam-summed data by way of an ultrasonic probe, wherein the beam-summed data comprises a plurality of steering angles;
  for each steering angle of the beam-summed data, segmenting the beam-summed data based on an axial imaging depth of the channel data;
    for each segment of the segmented beam-summed data:
      estimating an extrapolation filter, based on the segmented beam-summed data, the extrapolation filter having a filter order; and
      extrapolating, by an extrapolation factor, the segmented beam-summed data based on the extrapolation filter, thereby generating extrapolated beam-summed data; and
  coherently compounding the extrapolated beam-summed data across all segments, thereby generating the ultrasound image.

This method performs transmit extrapolation on the beam-summed data, thereby improving the contrast of the ultrasound image. The beam-sum data corresponds to data summed across the aperture for several transmit beams overlapping on a point of interest. In addition, this method provides an increase in ultrasound image frame rate and a reduction in motion artifacts in the final ultrasound image by retaining contrast and resolution with fewer actual transmit events. By estimating the extrapolation filter based on the segmented beam-summed data, the extrapolation filter may directly correspond to the beam-summed data. In this way, the accuracy of the extrapolation performed on the segmented beam-summed data is increased. In other words, this method predicts beam-summed data from transmit angles outside of the range of angles used to obtain the original beam-summed data by extrapolation.

In an embodiment, the method further comprises:

for each axial segment of the beam-summed data, applying a Fourier transform to an axial segment of the beam-summed data; and performing an inverse Fourier transform on the extrapolated beam-summed data.

By performing the extrapolation of the segmented beam-summed data in the temporal frequency domain, the accuracy of the extrapolated beam-summed data may be further increased.

In an arrangement, the beam-summed data is obtained by way of at least one of plane wave imaging and diverging wave imaging.

In this way, it is possible to produce an ultrafast ultrasound imaging method with increased image contrast and frame rate.

In some embodiments, the axial segment is less than 4 wavelengths in depth, for example less than or equal to 2 wavelengths in depth.

In this way, the performance of the system, which is largely dependent on the number of segments of beam-summed data to be extrapolated, may be improved whilst maintaining the improvement in image quality, which is inversely proportional to the size of the axial segment.

In some arrangements, the plurality of steering angles comprises less than 20 angles, for examples less than or equal to 10 angles.

In this way, the computational performance of the ultrasound system may be improved, as there are fewer steering angle to process, whilst maintaining the detail of the final ultrasound image, which is proportional to the number of steering angle used.

In some designs, the filter order is less than or equal to half the number of steering angles.

In an embodiment, the extrapolation factor is less than or equal to 10×, for example less than or equal to 8×.

In this way, it is possible to achieve a substantial improvement in the contrast resolution of the ultrasound image whilst preserving the speckle texture within the image.

In an arrangement, the estimation of the extrapolation filter is performed using an autoregressive model.

In an embodiment, the estimation of the extrapolation filter is performed using the Burg technique.

In this way, the extrapolation filter may be simply estimated without requiring a significant amount of processing power.

In an arrangement, the extrapolation occurs in the transmit direction.

According to examples in accordance with a further aspect of the invention, there is provided a computer program comprising computer program code means which is adapted, when said computer program is run on a computer, to implement the method defined above.

According to examples in accordance with a further aspect of the invention, there is provided a controller for controlling the generation of an ultrasound image, wherein the controller is adapted to:

obtain beam-summed data by way of an ultrasonic probe, wherein the beam-summed data comprises a plurality of steering angles;

for each steering angle of the beam-summed data, segment the beam-summed data based on an axial depth of the beam-summed data;

for each segment of the segmented beam-summed data:

estimate an extrapolation filter, based on the segmented beam-summed data, the extrapolation filter having a filter order; and extrapolate, by an extrapolation factor, the segmented beam-summed data based on the extrapolation filter, thereby generating extrapolated beam-summed data; and coherently compound the extrapolated beam-summed data across all segments, thereby generating the ultrasound image.

According to examples in accordance with a further aspect of the invention, there is provided an ultrasound system, the system comprising:

an ultrasonic probe;

a controller as defined above; and a display device for displaying the high contrast ultrasound image.

In an embodiment, the system further comprises a user interface having a user input.

In this way, it is possible for a user to provide an instruction to the ultrasound system.

In a further embodiment, the user input is adapted to adjust at least one of: the axial depth of the axial segment; the extrapolation factor; and the filter order.

In this way, the user may empirically adapt the various parameters of the extrapolation method in order to maximize the image quality according to their subjective opinion.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides methods and systems for generating an ultrasound image. In a method, the generation of an ultrasound image comprises: obtaining channel data, the channel data defining a set of imaged points; for each imaged point: isolating the channel data; performing a spatial spectral estimation on the isolated channel data; and selectively attenuating the spatial spectral estimation channel data, thereby generating filtered channel data; and summing the filtered channel data, thereby forming a filtered ultrasound image.

In some examples, the method comprises aperture extrapolation. The aperture extrapolation improves the lateral resolution of the ultrasound image. In other examples, the method comprises transmit extrapolation. The transmit extrapolation improves the contrast of the image. In addition, the transmit extrapolation improves the frame rate and reduces the motion artifacts in the ultrasound image. In further examples, the aperture and transmit extrapolations may be combined.

Figure 1:
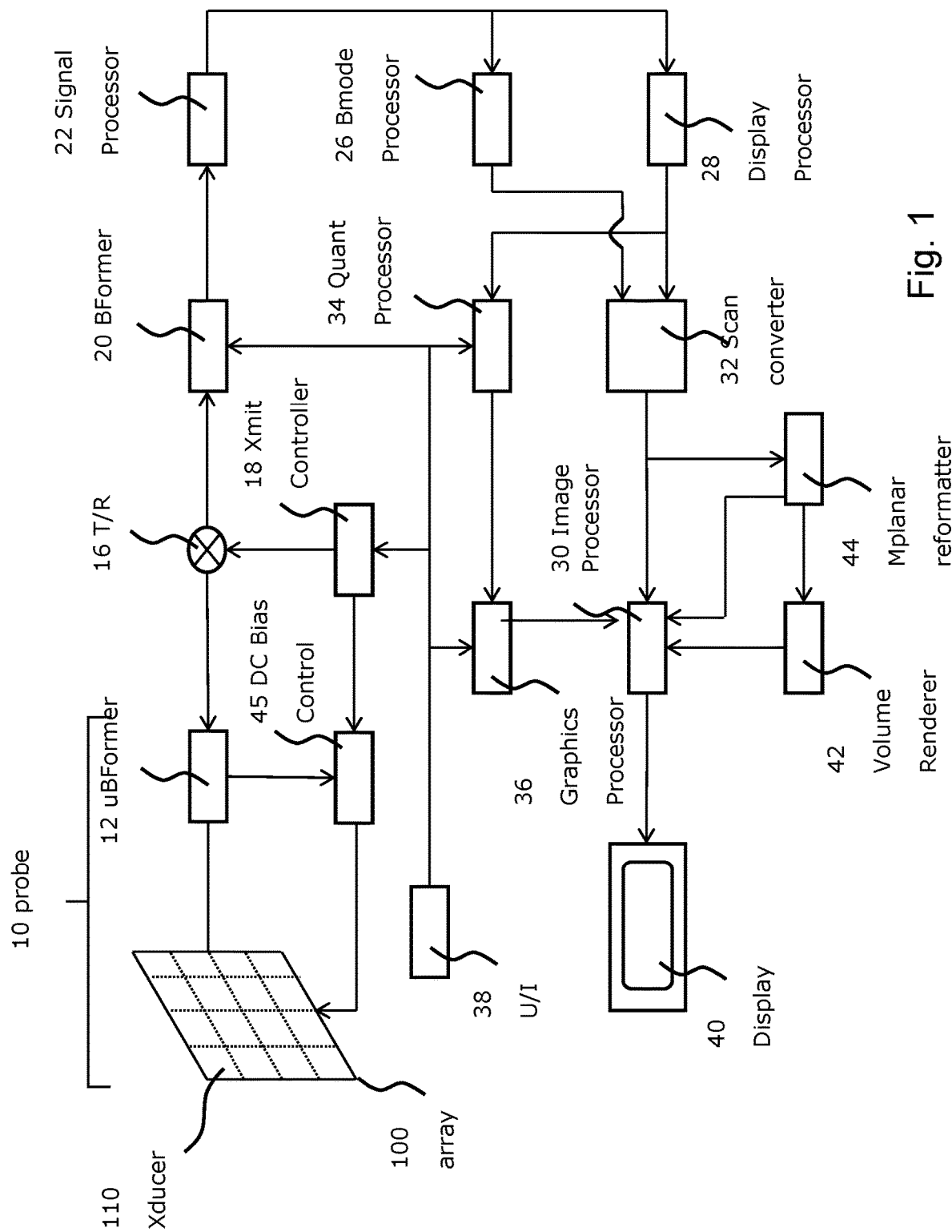
FIG. 1 shows an ultrasound diagnostic imaging system to explain the general operation.

The general operation of an exemplary ultrasound diagnostic imaging system will first be described, with reference to FIG. 1, and with emphasis on the signal processing function of the system since this invention relates to the processing of the signals measured by the transducer array.

The system comprises an array transducer probe 10 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The transducer array 100 is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasound beams from the transducer array 10 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducers are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 10' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 10' and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
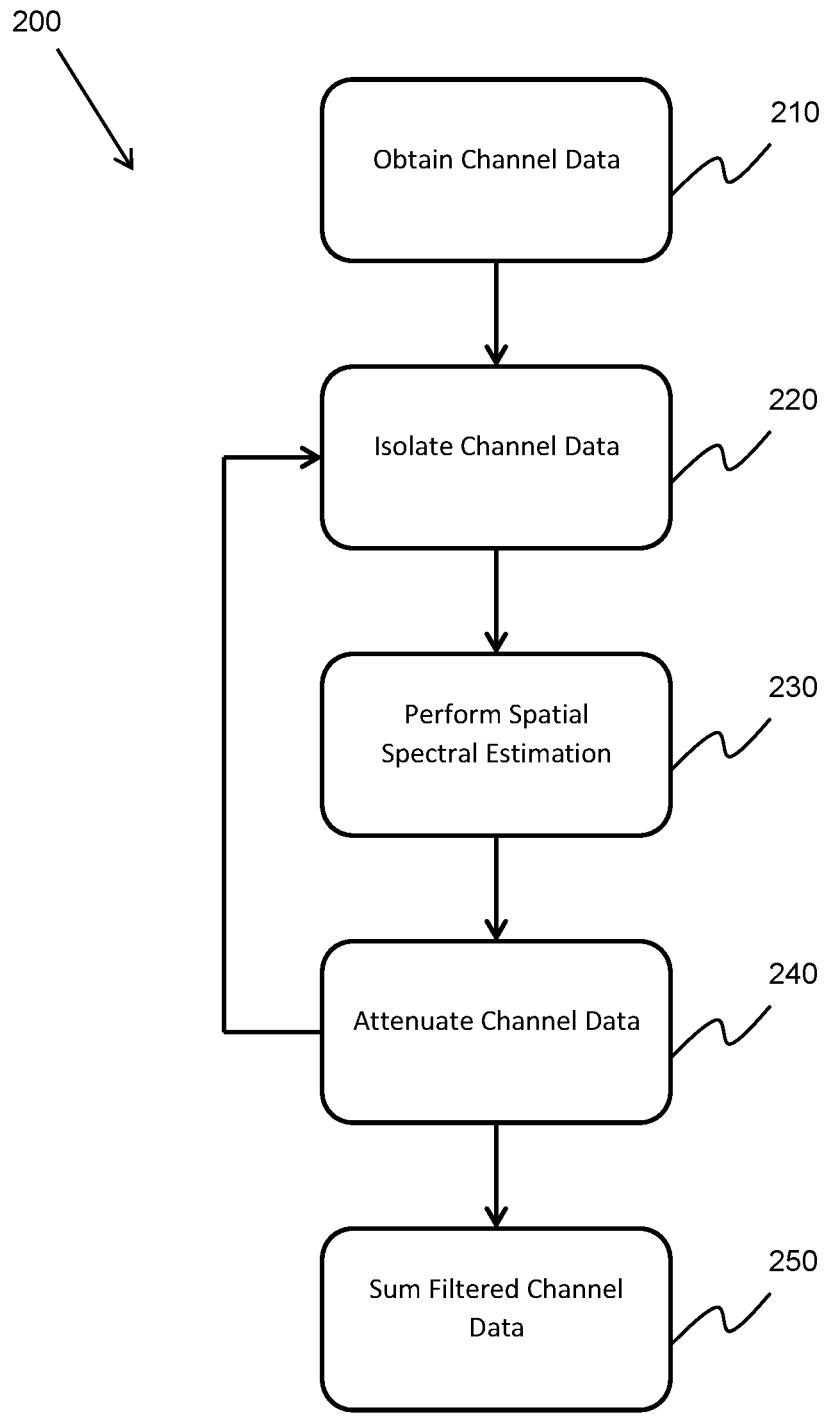
FIG. 2 shows a method of selectively attenuating channel data of an ultrasound image.

FIG. 2 shows a method 200 of performing selective attenuation on an ultrasound image.

In step 210, channel data is obtained from an ultrasonic probe. The channel data defines a set of imaged points within a region of interest.

In step 220, the channel data is isolated for a given imaged point, meaning that it may be operated on independently of the remaining channel data.

In step 230, a spatial spectral estimation is performed on the isolated channel data. For example, the channel data may be decomposed into a finite sum of complex exponentials as follows:

$$S(x) \approx \Sigma_{i=1}^{N} a_i e^{ik_i x},$$

where: x is the lateral coordinate along the array of transducer elements of the ultrasonic probe; S(x) is the measured channel data signal at x; N is the model order, which is the number of sinusoidal components used to describe the channel data; $a_i$ is the first model parameter; and $k_i$ is the second model parameter. Any spatial spectral estimation method may be performed on the isolated channel data. For example, a Fourier transform may be performed in combination with a Total Variation method. In another example, a complex L1/L2 minimization may be used to decompose the channel data signal as a sparse sum of off-axis and off-range components. In the example above, an autoregressive model is used.

In this case, the $a_i$ are complex parameters, wherein the phase may be between $-\pi$ and $\pi$ and wherein the modulus is a real, positive number, indicative of the strength of the channel data signal.

The $k_i$ may also theoretically be complex; however, in this example they are real numbers. They may theoretically range from $-\infty$ to $\infty$ but in practice, due to sampling restrictions; they range from $$-\frac{1}{dx} \text{ to } \frac{1}{dx},$$

where dx is the element spacing in the transducer array of the ultrasonic probe.

In this example, the first and second model parameters may be estimated through any known method in the art spectral estimation techniques. For example, the parameters may be estimated by way of a non-parametric method, such as a fast Fourier transform (FFT) or discrete Fourier transform (DFT), or a parametric method, such as the autoregressive (AR) or autoregressive moving average (ARMA) methods.

In step 240, the channel data is selectively attenuated by including an attenuation coefficient in the above formulation:

$$S_f(x) \approx \Sigma_{i=1}^{N} w(k_i) a_i e^{ik_i x},$$

where: $S_f(x)$ is the filtered channel data signal at x; and $w(k_i)$ is the attenuation coefficient, wherein $w(k_i)$ may be a real number $\leq 1$.

$w(k_i)$ is inversely proportional to $k_i$, meaning that at higher spatial frequencies, the value of $w(k_i)$ decreases, thereby attenuating the high spatial frequency clutter signals. In other words, the attenuation coefficient may be dependent on the spatial frequency of the channel data. The attenuation coefficient is applied across the entire spatial frequency spectrum of the channel data, thereby attenuating any high spatial frequency signals included within the channel data. $w(k_i)$ may, for example, be Gaussian in shape as shown in the following equation:

$$w(k_i) = e^{-k_i^2/k_0^2},$$

where $k_0$ is an additional parameter, which dictates the width of the Gaussian and so the aggressiveness of the high spatial frequency signal attenuation. For lower values of $k_0$, the Gaussian is thinner and so the clutter filtering is more aggressive. For larger values of $k_0$, the width of the Gaussian is increased leading to less aggressive clutter filtering, which in turn allows more signals to contribute to the final ultrasound image. In this example, the value of $k_0$ may be selected to be of the order of magnitude of the inverse of the aperture size, for example $$k_0 = \frac{\pi}{a},$$

where a is me aperture size. In addition, the value of $k_0$ may be altered depending on the axial depth of the current channel data segment.

Alternative functions may also be used as an attenuation coefficient. For example, it may be possible to estimate the angular transmit, or round-trip, beampattern of the channel data, such as through simulation, to use as a weighting mask. Further, a rectangular function may be used, wherein the width of the function dictates a cutoff frequency above which all signals are rejected. Further still, an exponential decay function may also be used.

Steps 220 to 240 are repeated for each axial segment of the channel data. When the final segment of channel data has undergone selective attenuation, the method may progress to step 250.

In step 250, the filtered channel data is summed to form the final clutter filtered ultrasound image.

Figure 3:
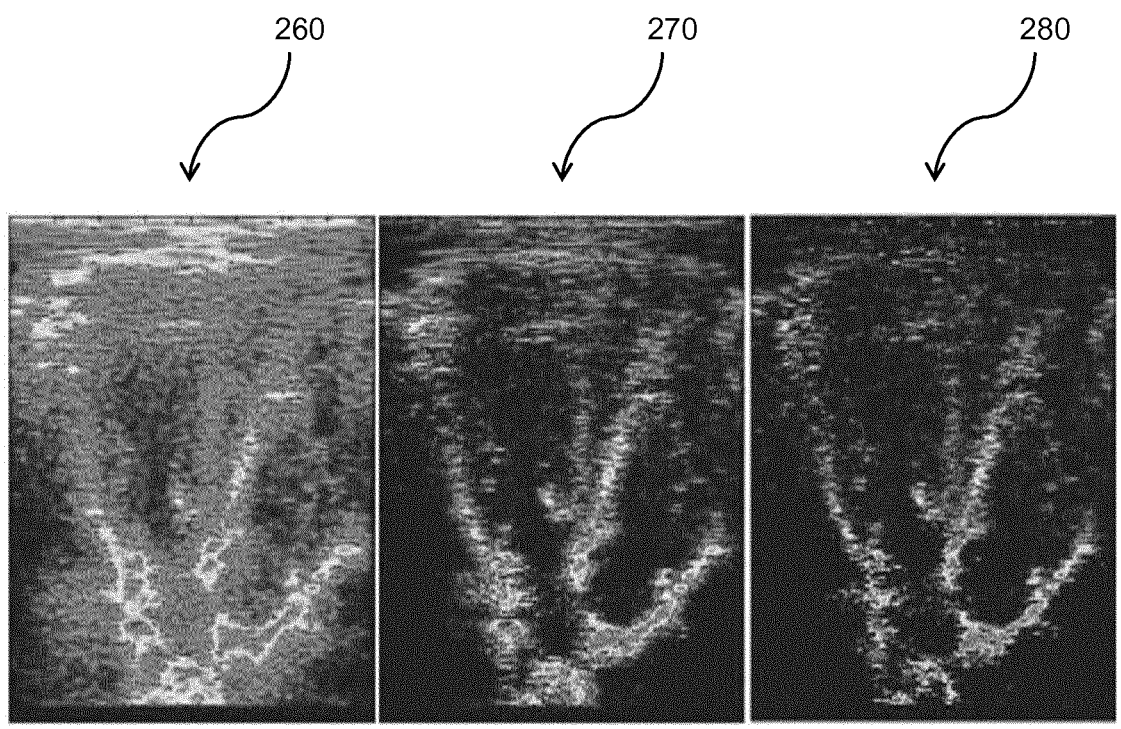
FIG. 3 shows an illustration of the implementation of the method of FIG. 2.

FIG. 3 shows a comparison between an ultrasound image of a heart at various stages in the method describe above with reference to FIG. 2.

The first image 260 shows the original ultrasound image captured from the raw channel data. As can be seen, the image contains a high level of noise and the details are difficult to make out.

The second image 270 shows the ultrasound image at stage 230 of the method, where the image has been reconstructed with the sparse sinusoidal decomposition as described above. In this example, the order of the model, N=4, meaning that the channel data at each depth is modeled as a sum 4 of sinusoids. The improvement in image clarity can already be seen; however, the signal is still noisy and the finer details, particularly towards the top of the image, remain largely unclear.

The third image 280 shows the ultrasound image at stage 250 of the method, after the application of the selective attenuation, thereby eliminating the sinusoidal signals with the highest spatial frequencies. As can be seen from the image, the signal noise has been significantly reduced by the attenuation of the high spatial frequency signals.

Figure 4:
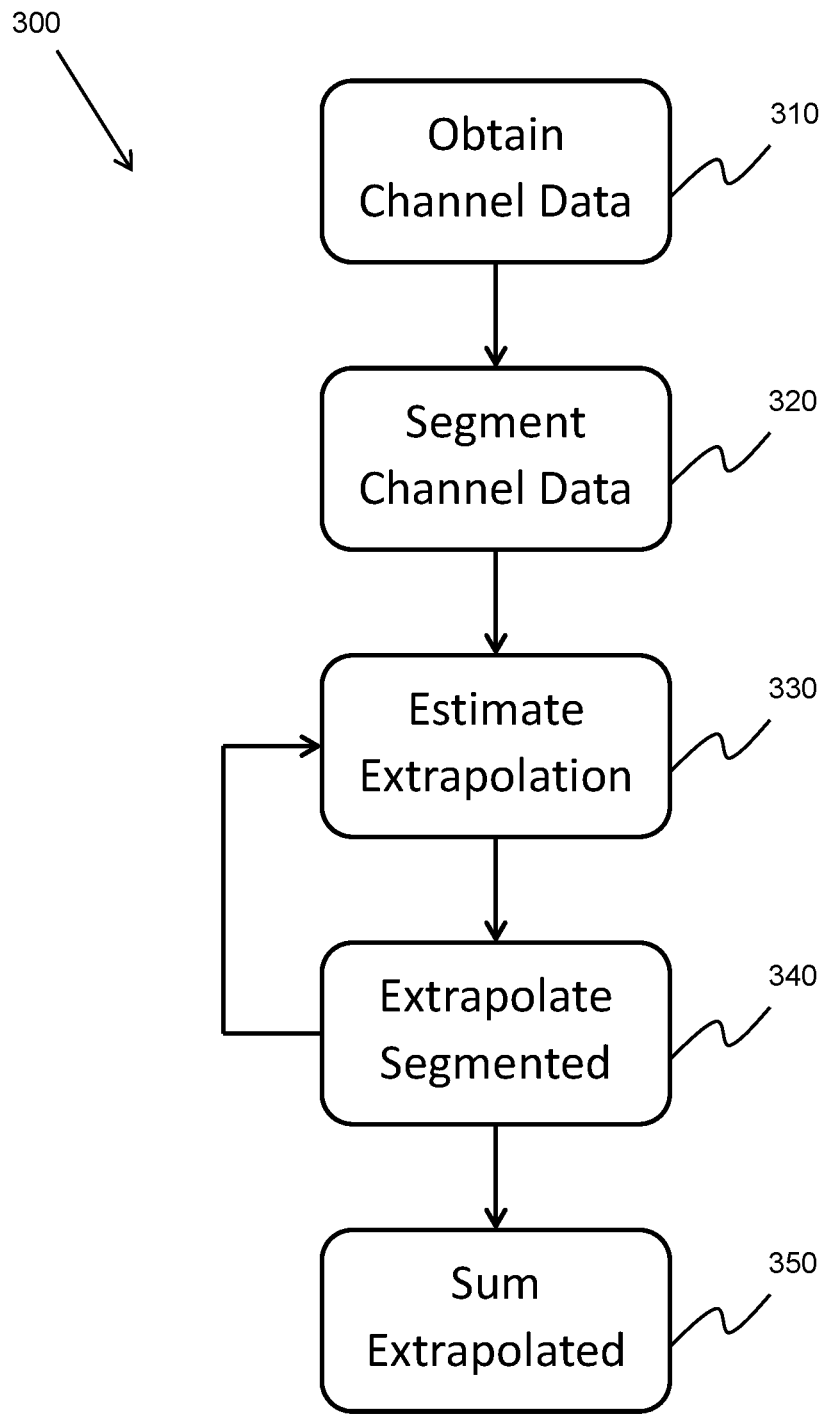
FIG. 4 shows a method of performing aperture extrapolation on an ultrasound image.

FIG. 4 shows a method 300 for applying aperture extrapolation to an ultrasound image.

In step 310, channel data is obtained by way of an ultrasonic probe.

In step 320, the channel is segmented based on an axial imaging depth of the axial data.

The axial window size of the segmented channel data may be empirically determined to suit the visual preferences of the user. For example, an axial window size of in the range of 1-2 wavelengths may produce a preferred image quality improvement. A larger axial window may provide a more reliable improvement in image quality and better preservation of speckle texture; however, it may adversely affect the axial resolution of the ultrasound image.

In step 330, an extrapolation filter of order p, $a_j$ where $1 \leq j \leq p$, is estimated based on the segmented channel data. In this case, the extrapolation filter may be estimated by way of the well-known Burg technique for autoregressive (AR) parameter estimation.

In step 340, the segmented channel data is extrapolated using the extrapolation filter estimated in step 330. In this case, a 1-step linear prediction extrapolator to obtain the 1$^{st}$ forward-extrapolated sample $X_{N+1}$, using the extrapolation filter and the previous p samples, as shown below:

$$X_{N+1} = \Sigma_{j=1}^{p} X_{N+1-j} a_j,$$

where: $X_N$ is the current sample; $X_{N+1}$ is the forward-extrapolated sample; and p is the order of the extrapolation filter, $a_j$.

The forward extrapolation may be generalized as follows:

$$X_k = \Sigma_{j=1}^{p} X_{k-j} a_j, k > N \qquad \text{(Forward Extrapolation)},$$

where k is the number of forward extrapolations performed.

By reversing the filter order and taking the complex conjugate of the filter coefficients, it is possible to backward-extrapolate the value up to the k$^{th}$ channel as a linear combination of the first p channels:

$$X_k = \Sigma_{j=1}^{p} X_{k+j} a_j^*, k < 1 \qquad \text{(Backward Extrapolation)}$$

Using both the forward and backward extrapolation formulae, it is possible to fully extrapolate the segmented channel data. Steps 330 and 340 are repeated for each axial segment of the segmented channel data.

In step 350, the fully extrapolated channel data segments are summed to obtain the beamsum signal and generate the final ultrasound image.

Figure 5:
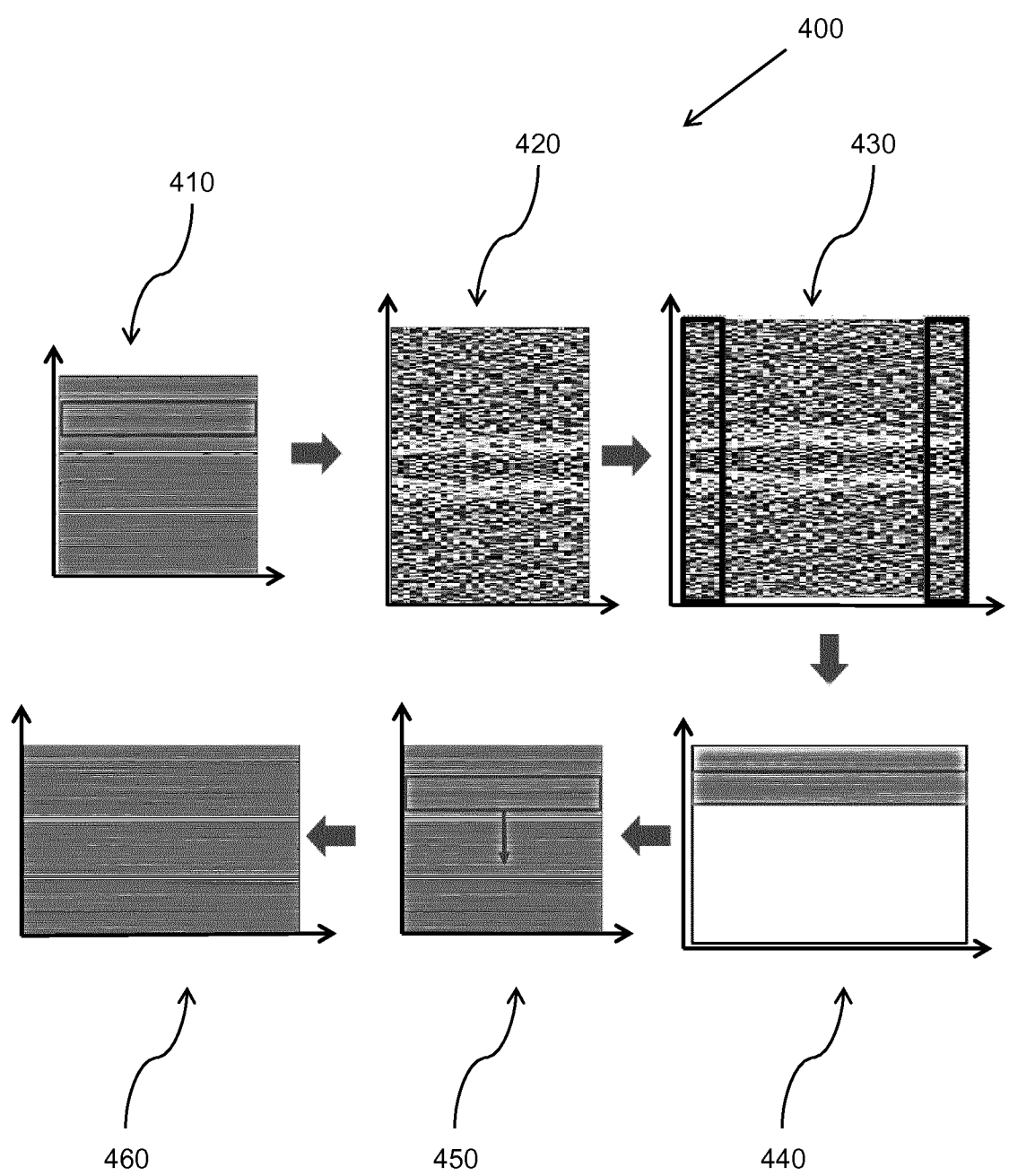
FIG. 5 shows an illustration of the method of FIG. 4.

FIG. 5 shows an illustration 400 of an embodiment of the method of FIG. 4.

In step 410, channel data is obtained by way of an ultrasonic probe. The plot shows signal intensity, by way of the shading, for each channel at a given axial depth. In the plots of steps 410, 440, 450 and 460, the horizontal axis represents the channel being measured and the vertical axis represents the axial depth of the measured channel data, wherein the axial depth is inversely proportional to the height of the vertical axis. In the plots of steps 420 and 430, the horizontal axis represents the channel being measured and the vertical axis represents the temporal frequency of the channel data.

In step 420, a fast Fourier transform (FFT) is applied to the channel data, thereby transforming the channel data into the temporal frequency domain. In this case, the extrapolation filter is also estimated in the temporal frequency domain. The estimation is once again performed by the Burg technique.

In step 430, the estimated extrapolation filter is used to extrapolate the temporal frequency domain channel data beyond the available aperture. The extrapolated data is highlighted by the boxes to the right, representing the forward extrapolated channel data, and the left, representing the backward extrapolated channel data, of the plot.

In step 440, an inverse Fourier transform is applied to the extrapolated temporal frequency channel data, thereby generating spatial channel data. As can be seen from the plot, the channel data now covers a wider aperture than in step 410.

In step 450, the axial window is moved to a new axial segment and steps 420 to 440 are repeated.

In step 460, the fully extrapolated channel data is obtained. This may then be used to generate the final ultrasound image.

FIGS. 6 to 11 show examples of the implementation of embodiments of the method of FIG. 4.

Figure 6:
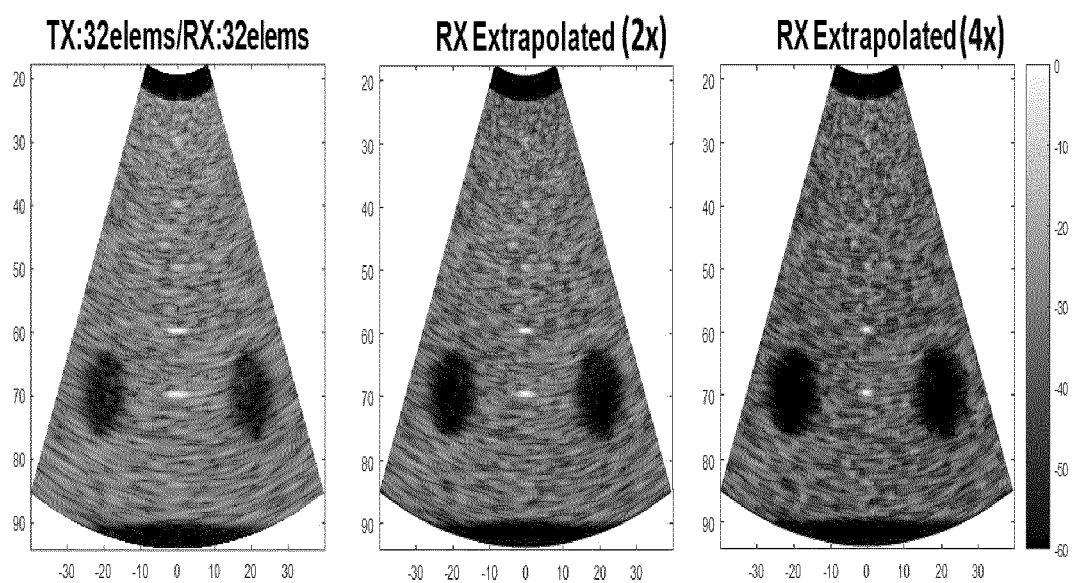
FIGS. 6 to 9 show examples of the implementation of the method of FIG. 4.
Figure 7:
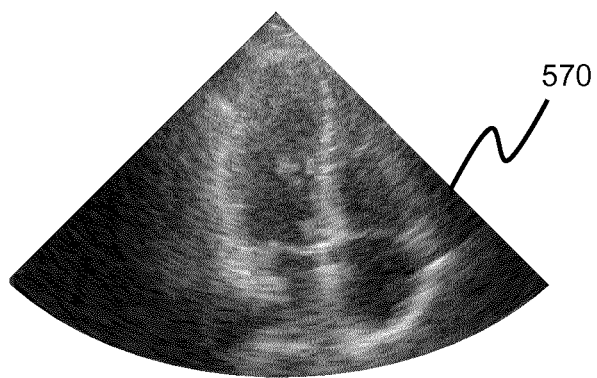
Figure 7:
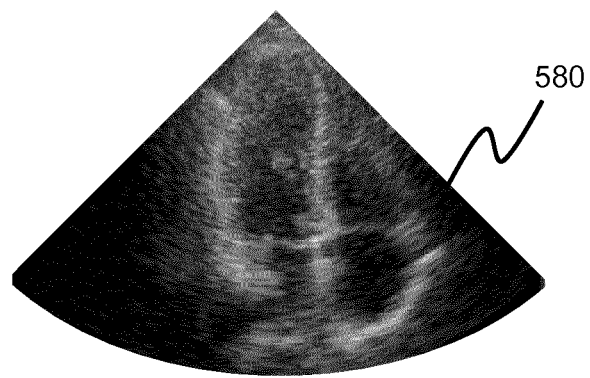
Figure 8:
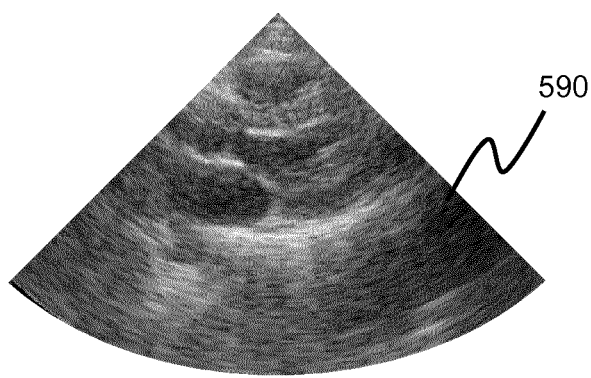
Figure 8:
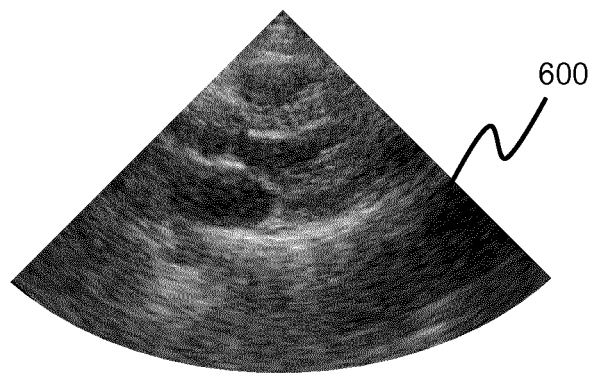

FIG. 6 shows a comparison between an ultrasound image before and after the implementation of two embodiments of the method of FIG. 4. In FIGS. 6 to 8, the horizontal axes of the images represent the lateral position, measured in mm, of the signals and the vertical axes represent the axial position, measured in mm, of the signals. The gradient scales indicate the signal intensity at a given signal location.

The first image 500 shows a conventional delay and sum (DAS) beamformed image of a simulated phantom. In this case, a 32-element aperture was used in both transmit and receive steps. As can be seem from the image, the two simulated cysts introduce heavy scattering and cause a large amount of noise in the ultrasound image. This results in the cysts appearing poorly defined and unclear.

The second image 510 shows the same ultrasound image after the application of the aperture extrapolation technique described above. In this case, the receive aperture was extrapolated by a factor of 2 using an extrapolation filter of order 4. As can be seen from the image, the extrapolation has substantially improved the lateral resolution of the image whilst maintaining the quality of the speckle texture.

The third image 520 once again shows the same ultrasound image after the application of the aperture extrapolation technique described above; however, in this case, the receive aperture was extrapolated by a factor of 4 using an extrapolation filter of order 4. As can be seen from the image, the extrapolation by this additional factor has further increased the lateral resolution of the ultrasound image.

FIGS. 7 and 8 show a comparison between an ultrasound image before and after the application of an aperture extrapolation method as described above. The images are shown in the 60 dB dynamic range.

In both cases, the top images, 570 and 590, show a conventional DAS beamformed cardiac image. The bottom images, 580 and 600, show the ultrasound images after an aperture extrapolation by a factor of 8. In both Figures, it can be seen that the aperture extrapolation leads to an improvement in both lateral resolution and image contrast.

Figure 9:
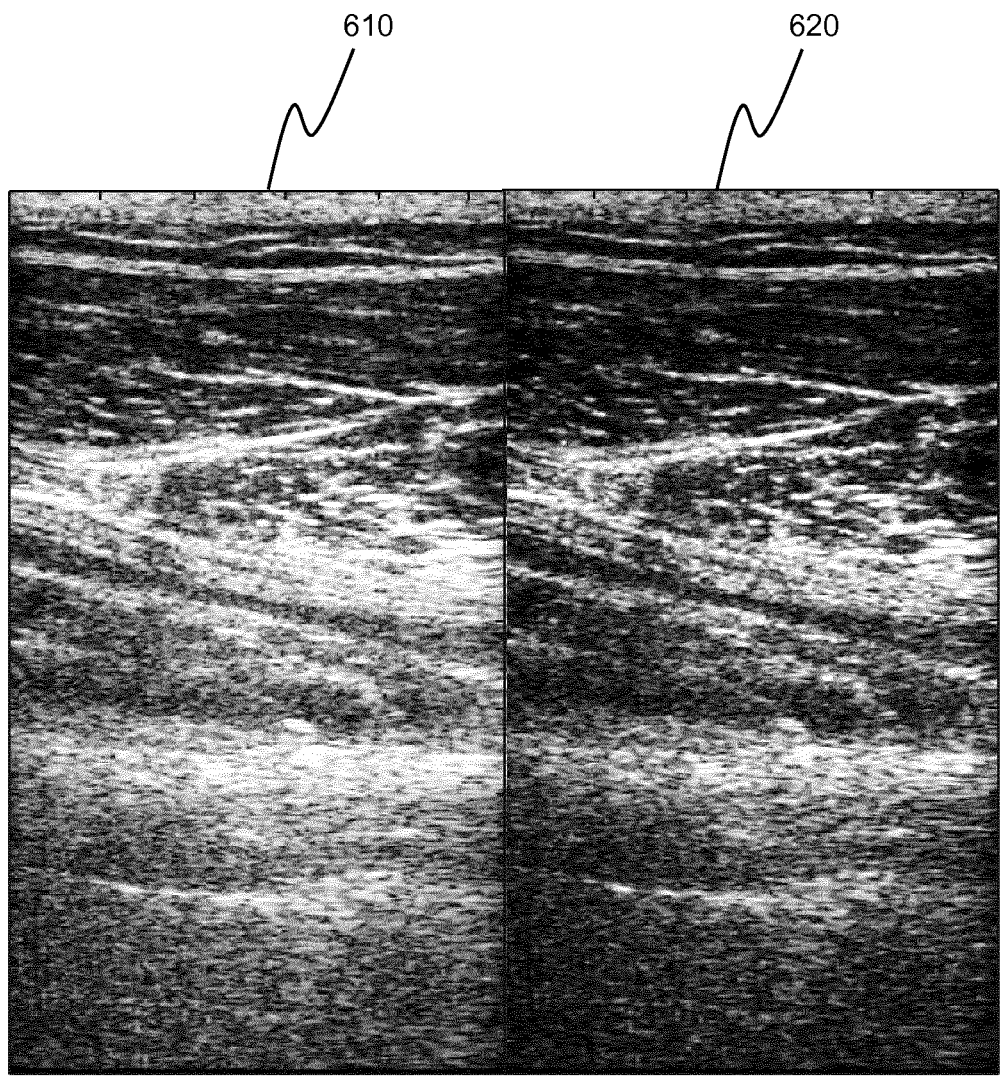

FIG. 9 shows a comparison between an ultrasound image of a leg before and after the application of an aperture extrapolation method as described above. The images are shown in the 60 dB dynamic range.

The first image 610 shows a conventional DAS beamformed ultrasound image. The second image 620 shows the same ultrasound image after the application of an aperture extrapolation method as described above. The aperture was extrapolated by a factor of 8. As can be seen from the second image, the aperture extrapolation leads to an improvement in the lateral resolution of the ultrasound image.

FIGS. 6 to 9 show an improvement in lateral resolution due to the aperture extrapolation method across a wide variety of imaging scenarios.

Figure 10:
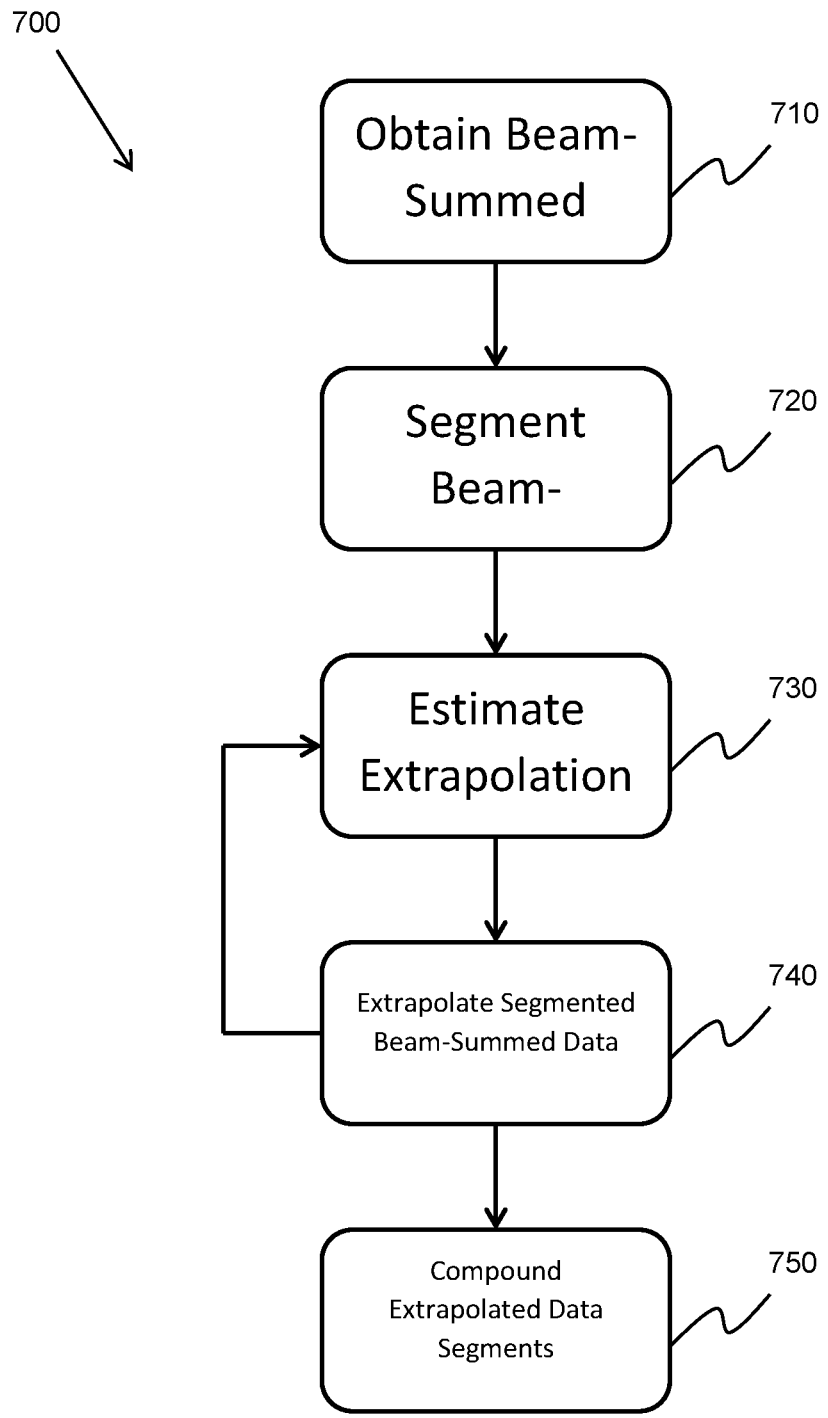
FIG. 10 shows a method of performing transmit extrapolation on an ultrasound image.

FIG. 10 shows a method 700 for applying transmit extrapolation to an ultrasound image.

In step 710, beam-summed data is obtained by way of an ultrasonic probe, wherein the beam-summed data comprises a plurality of steering angles.

In step 720, the beam-summed data is segmented for each steering angle based on the axial depth of the beam-summed data.

In step 730, an extrapolation filter of order p, $\alpha_j$ where $1 \leq j \leq p$, is estimated based on the segmented beam-summed data. In this case, the extrapolation filter may be estimated by way of the well-known Burg technique for autoregressive (AR) parameter estimation.

In step 740, the segmented beam-summed data is extrapolated using the extrapolation filter estimated in step 730. In this case, a 1-step linear prediction extrapolator to obtain the $1^{st}$ forward-extrapolated sample $X_{N+1}$, using the extrapolation filter and the previous p samples of the available transmit angles, as shown below:

$$X_{N+1} = \Sigma_{j=1}^{p} X_{N+1-j} \alpha_j,$$

where: $X_N$ is the current sample; $X_{N+1}$ is the forward-extrapolated sample; and p is the order of the extrapolation filter, $\alpha_j$.

The forward extrapolation may be generalized as follows:

$$X_k = \Sigma_{j=1}^{p} X_{k-j} \alpha_j, k > N \quad \text{(Forward Extrapolation)},$$

where k is the number of forward extrapolations performed.

By reversing the filter order and taking the complex conjugate of the filter coefficients, it is possible to backward-extrapolate the value up to the $k^{th}$ transmit angle as a linear combination of the first p transmit angles:

$$X_k = \Sigma_{j=1}^{p} X_{k+j} \alpha_j^*, k < 1 \quad \text{(Backward Extrapolation)}$$

Using both the forward and backward extrapolation formulae, it is possible to fully extrapolate the segmented beam-summed data. Steps 730 and 740 are repeated for each axial segment of the segmented beam-summed data.

In step 750, the fully extrapolated beam-summed data segments are coherently compounded to obtain the final beamsum signal and generate the final ultrasound image.

The transmit scheme used in the above method may be: planar; diverging; single-element; or focused.

Figure 11:
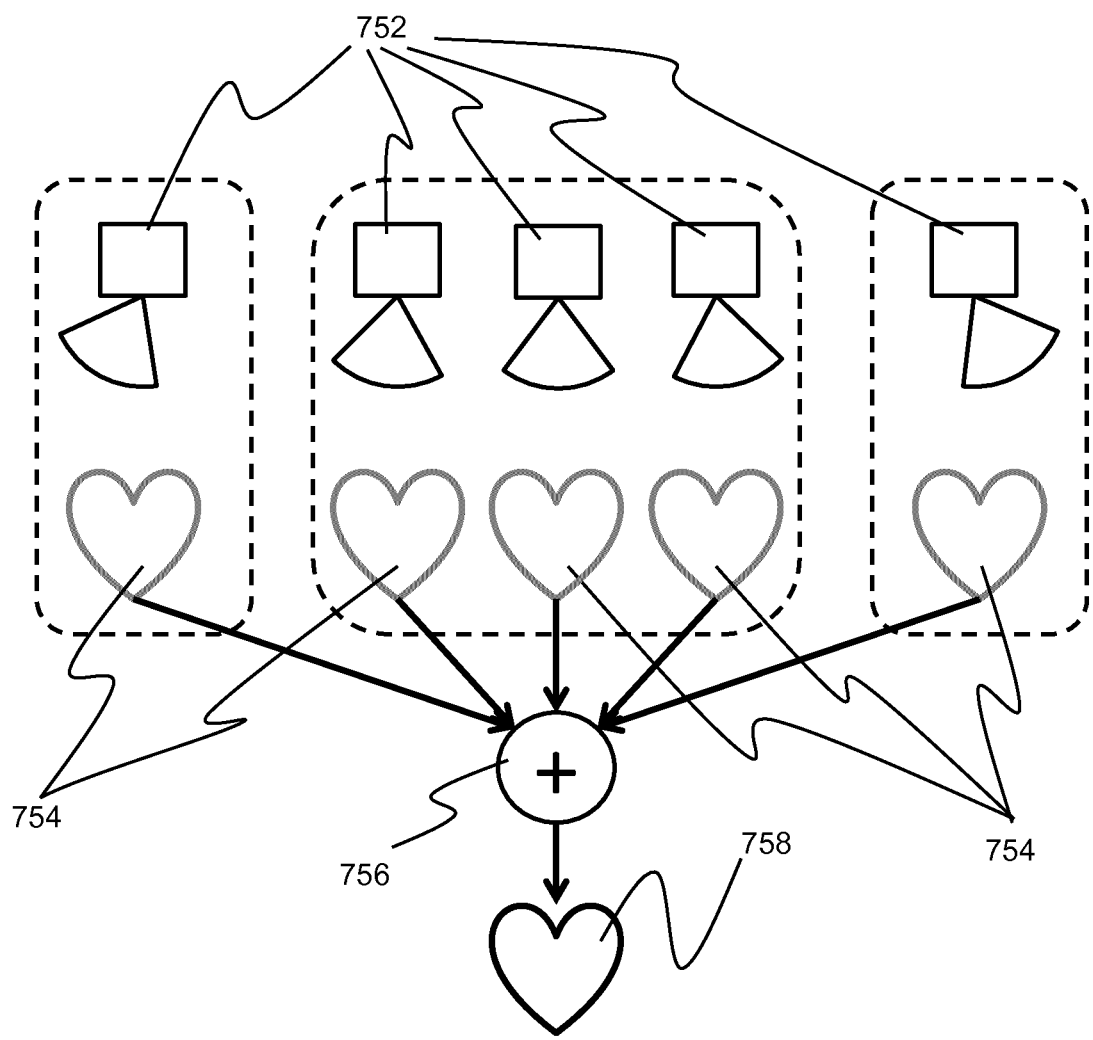
FIG. 11 shows an illustration of the method of FIG. 10.

FIG. 11 shows an illustration of the method of FIG. 10. For each of a plurality of steering angles 752, a low contrast ultrasound image 754 is obtained. By coherently compounding 756 the plurality of low contrast ultrasound images, it is possible to generate a single high contrast ultrasound image 758. The improvement in image contrast is proportional to the number of steering angles used, and so the number of low contrast ultrasound images coherently compounded to generate the high contrast ultrasound image; however, a large number of initial steering angles may result in a decreased computational performance of the ultrasound system. By extrapolating from a small number of initial steering angles, it is possible to increase the image contrast without significantly degrading the performance of the ultrasound system.

Figure 12:
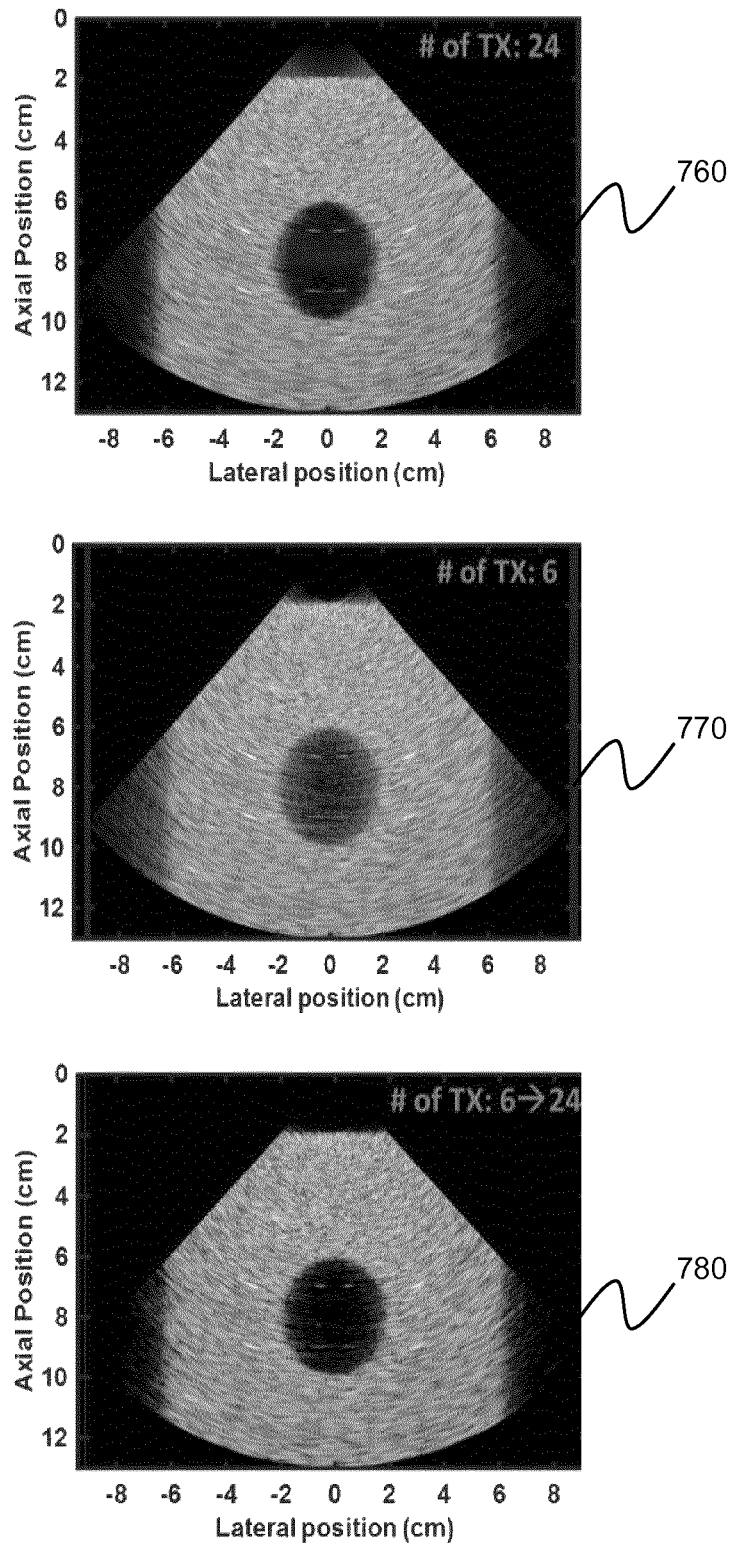
FIGS. 12 to 14 show examples of the implementation of the method of FIG. 10.

FIG. 12 shows a comparison between an ultrasound image before and after the implementation of the transmit extrapolation and a reference image.

The first image 760 shows a reference image of a simulated phantom containing a 40 mm diameter anechoic cyst lesion. The phantom contains 4 strong point scatterers in the speckle background and 4 weak point scatterers inside of the anechoic lesion.

The image was formed using 24 diverging waves.

The second image 770 shows an image of the same simulated phantom formed from only the 6 central angles of the 24 steering angles of the reference image. The 24 steering angles are evenly spaced between −45° and 45°, meaning that the central 6 steering angles are separated by an angle of 3.91°. It is clear to see from this image that the reduced number of steering angles results in a lower image contrast.

The third image 780 shows the result of applying the transmit extrapolation described above to the second image 770. In this case, an extrapolation filter of order 3 was used to extrapolate the number of transmit angles by a factor of 4. The image is generated by coherently compounding the data from the initial 6 transmit angles with the 18 predicted beamsum data from the extrapolation. As can be seen from the third image, the contrast is significantly improved from the second image and is comparable to that of the reference image. In addition, the contrast enhancement does not result in any artifacts suppressing the weak point scatterers inside the anechoic lesion.

Figure 13:
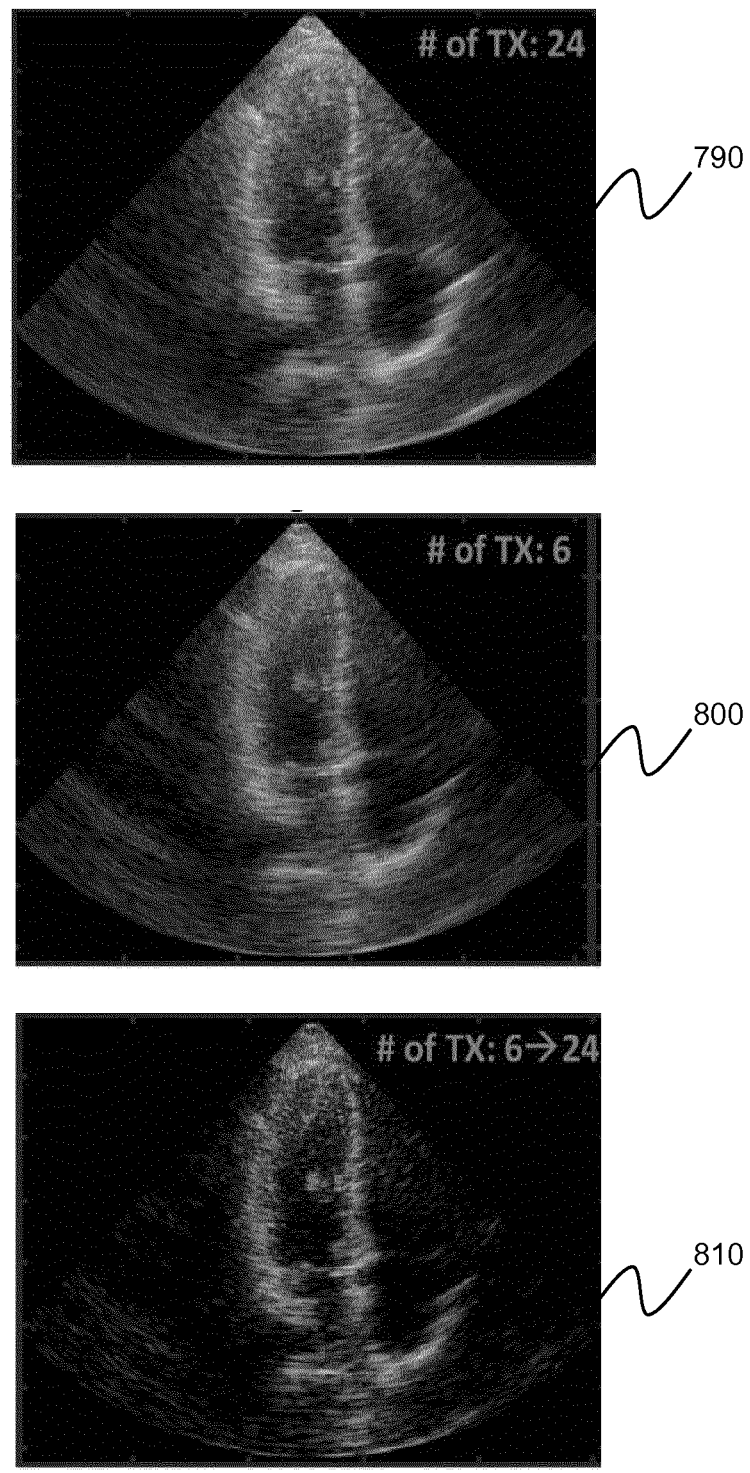

FIG. 13 shows a comparison between an ultrasound image before and after the implementation of the transmit extrapolation and a reference image.

The first image 790 shows a reference image of an apical 4-chamber view of the heart form a patient. The image was formed using 24 diverging waves.

The second image 800 shows an image of the same data set formed with only 6 diverging waves. As before, the 6 diverging waves were selected as the central 6 of the 24 steering angles. As can be seen from the image, the image contrast of the second image is significantly lower than that of the first image.

The third image 810 shows the result of applying a transmit extrapolation to the second image as described above. In this case, an extrapolation filter of order 3 was used to extrapolate the number of steering angles by a factor of 4. Once again, the image is generated by coherently compounding the data from the initial 6 transmit angles with the 18 predicted beamsum data from the extrapolation. It is clear to see from the third image that the image contrast has been improved by the transmit extrapolation.

Figure 14:
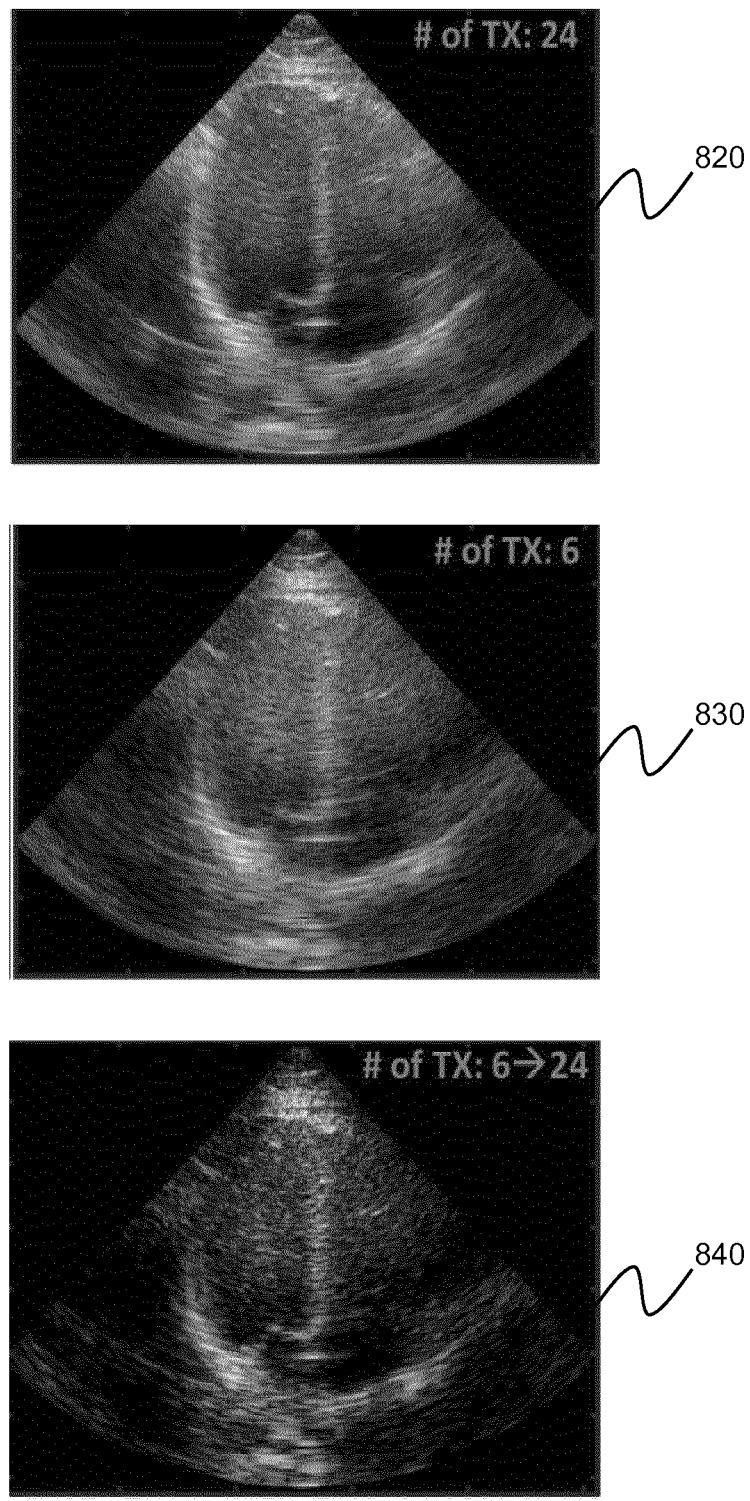

FIG. 14 shows a comparison between an ultrasound image before and after the implementation of the transmit extrapolation and a reference image.

The first image 820 shows a reference image of an apical 4-chamber view of the heart from a different patient to FIG. 13. The image was formed using 24 diverging waves. Unlike FIG. 13, the initial reference image for this patient has a poor image contrast.

The second image 830 shows an image of the same data set formed with only 6 diverging waves. As before, the 6 diverging waves were selected as the central 6 of the 24 steering angles. As can be seen from the image, the image contrast of the second image is significantly lower than that of the first image, which in this case renders a lot of the finer detail extremely unclear.

The third image 840 shows the result of applying a transmit extrapolation to the second image as described above. In this case, an extrapolation filter of order 3 was used to extrapolate the number of steering angles by a factor of 4. Once again, the image is generated by coherently compounding the data from the initial 6 transmit angles with the 18 predicted beamsum data from the extrapolation. It is clear to see from the third image that the image contrast has been improved by the transmit extrapolation.

It should be noted that any combination of extrapolation factor and extrapolation filter order may be used in any of the methods described above. In addition, any number of steering angles may be selected in the final method.

In some ultrasound systems, a combination of the above methods may be employed in order to further increase the image quality of the final ultrasound image.

For example, the aperture extrapolation method, described with reference to FIGS. 4 to 9, may be performed on a set of channel data followed by the transmit extrapolation method, described with reference to FIGS. 10 to 14. In this case, the aperture extrapolation may be performed for each transmit signal of the ultrasonic probe and the extrapolated channel data summed over the aperture, thereby generating a set of aperture extrapolated channel data. Following the summation, the transmit extrapolation may be performed on the aperture extrapolated channel data. In this way, the lateral resolution and image contrast of the final ultrasound image may be improved. In addition, for PWI and DWI ultrasound systems, the use of the transmit extrapolation method may allow for an increase in the frame rate of the ultrasound image.

In another example, the transmit extrapolation method may be performed before the aperture extrapolation method. In this case, the transmit extrapolation may be performed for each transducer element of the ultrasonic probe and the extrapolated channel data summed over all transmit angles, thereby generating a set of transmit extrapolated channel data. The aperture extrapolation method may then be performed over the transmit extrapolated channel data.

In both cases, the selective attenuation method, described with reference to FIGS. 2 and 3, may be employed to reduce the amount of off-axis clutter in the final ultrasound image. As this method simply attenuates the signals possessing a high spatial frequency, it may be performed in any order with the aperture extrapolation and transmit extrapolation methods. Alternatively, the selective attenuation method may be combined with only the aperture extrapolation method or the transmit extrapolation method.

It should be noted that the signals used to form the channel, and beam-summed, data may be geometrically aligned prior to performing the methods described above.

As discussed above, embodiments make use of a controller for performing the data processing steps.

The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for performing off-axis clutter filtering in an ultrasound image, the method comprising:
   obtaining channel data from an ultrasonic probe defining a set of imaged points, wherein the ultrasonic probe comprises an array of transducer elements;
   for each imaged point in a region of interest:
      isolating the channel data associated with said imaged point;
      performing a spatial spectral estimation of the isolated channel data to identify one or more spatial-frequency components of the isolated channel data; and
      selectively attenuating the one or more spatial-frequency components of the isolated channel data by way of an attenuation coefficient based on the spatial spectral estimation, thereby generating filtered channel data; and summing the filtered channel data associated with each imaged point of said set of imaged points, thereby generating a filtered ultrasound image.

2. The method of claim 1, wherein the isolating of the channel data comprises processing a plurality of observations of the imaged point.

3. The method of claim 1, wherein the spatial spectral estimation comprises decomposing the channel data into a finite sum of complex exponentials.

4. The method of claim 3, wherein the complex exponentials comprise:
a first model parameter; and
a second model parameter.

5. The method of claim 4, wherein the first model parameter is complex.

6. The method of claim 4, wherein the second model parameter is inversely proportional to the distance between adjacent transducer elements of the ultrasonic probe.

7. The method of claim 4, wherein the first and second model parameters are estimated by way of spatial spectral estimation.

8. The method of claim 4, wherein the attenuation coefficient is dependent on the second model parameter.

9. The method as claimed in claim 1, wherein the attenuation coefficient is Gaussian.

10. The method of claim 1, wherein the attenuation coefficient is depth dependent.

11. The method of claim 1, wherein the attenuation coefficient is adapted to attenuate the channel data to half the width of a receive beampattern.

12. The method of claim 1, wherein the spatial spectral estimation is based on an autoregressive model.

13. A non-transitory computer-readable medium comprising processor-executable instructions for performing off-axis clutter filtering in an ultrasound image, which when executed cause a processor or controller to:
obtain channel data from an ultrasonic probe defining a set of imaged points, wherein the ultrasonic probe comprises an array of transducer elements;
for each imaged point in a region of interest:
isolate the channel data associated with said imaged point;
perform a spatial spectral estimation of the isolated channel data to identify one or more spatial-frequency components of the isolated channel data; and
selectively attenuate the one or more spatial-frequency components of the isolated channel data by way of an attenuation coefficient based on the spatial spectral estimation, thereby generating filtered channel data; and
sum the filtered channel data associated with each imaged point of said set of imaged points, thereby generating a filtered ultrasound image.

14. A controller for controlling the filtering of off-axis clutter in an ultrasound image, wherein the controller is adapted to:
obtain channel data from an ultrasonic probe defining a set of imaged points;
for each imaged point in a region of interest:
isolate the channel data associated with said imaged point;
perform a spatial spectral estimation of the isolated channel data to identify one or more spatial-frequency components of the isolated channel data; and
selectively attenuate the one or more spatial-frequency components of the isolated channel data by way of an attenuation coefficient based on the spatial spectral estimation, thereby generating filtered channel data; and
sum the filtered channel data associated with each imaged point of said set of imaged points, thereby generating a filtered ultrasound image.

15. An ultrasound system, the system comprising:
an ultrasonic probe, the ultrasonic probe comprising an array of transducer elements;
a controller as claimed in claim 14; and
a display device for displaying the filtered ultrasound image.

* * * * *